United States Patent
Dong et al.

(10) Patent No.: US 10,422,011 B2
(45) Date of Patent: Sep. 24, 2019

(54) MOLECULAR IDENTIFICATION METHOD FOR SINGLE DINOFLAGELLATE CYST

(71) Applicant: South China Environmental Monitoring Center, State Oceanic Administration, Guangzhou (CN)

(72) Inventors: Yanhong Dong, Guangzhou (CN); Aibin Zhan, Beijing (CN); Yangchun Gao, Beijing (CN); Hongda Fang, Guangzhou (CN); Haitao Li, Guangzhou (CN)

(73) Assignee: South China Environmental Monitoring Center, State Oceanic Administration, Guangzhou (CN)

(*) Notice: Subject to any disclaimer, the term of this patent is extended or adjusted under 35 U.S.C. 154(b) by 0 days.

(21) Appl. No.: 15/816,571

(22) Filed: Nov. 17, 2017

(65) Prior Publication Data
US 2018/0282823 A1 Oct. 4, 2018

(30) Foreign Application Priority Data

Nov. 17, 2016 (CN) .......................... 2016 1 1003715
May 10, 2017 (CN) .......................... 2017 1 0323825

(51) Int. Cl.
*C12Q 1/6893* (2018.01)
*C12Q 1/6809* (2018.01)
*C12Q 1/6806* (2018.01)
*C12Q 1/686* (2018.01)
*C12Q 1/6811* (2018.01)

(52) U.S. Cl.
CPC .......... *C12Q 1/6893* (2013.01); *C12Q 1/6806* (2013.01); *C12Q 1/6809* (2013.01); *C12Q 1/6811* (2013.01); *C12Q 1/686* (2013.01)

(58) Field of Classification Search
None
See application file for complete search history.

(56) References Cited

PUBLICATIONS

Tada et al. Cancer Research 1990; 50: 1121-1124 (Year: 1990).*
Gao et al. PeerJ 2017; 5: e3224 (Year: 2017).*
(Continued)

*Primary Examiner* — Angela M. Bertagna
(74) *Attorney, Agent, or Firm* — Wayne & Ken, LLC; Tony Hom (57) ABSTRACT

The present invention provides a molecular identification method for a single dinoflagellate cyst, including: obtaining crushed liquids of the single dinoflagellate cyst; performing a first PCR amplification with the crushed liquids as a template, SEQ ID NO: 1 (GTCCGCCCTCTGGGTG) as a forward primer, and SEQ ID NO: 2 (TCGCAGTAGT-SYGTCTTTAAC) as a reverse primer to obtain an amplification product so as to determine the species of the dinoflagellate cyst. If the first amplification product is unsuitable for sequencing due to weak bands by electrophoresis detection, a second (nested) PCR amplification and sequencing is performed with SEQ ID NO: 1 (GTCCGC-CCTCTGGGTG) as a forward primer and SEQ ID NO: 2 (TCGCAGTAGTSYGTCTTTAAC) as a reverse primer to determine the species of dinoflagellate.

3 Claims, 3 Drawing Sheets

Specification includes a Sequence Listing.

(56) References Cited

PUBLICATIONS

Innis, M.A. and Gelfand, D.H. (1990). Optimization of PCRs. In M.A. Innis, D.H. Gelfand, J.J. Sninsky, & T.J. White (Eds.), PCR Protocols: A Guide to Methods and Applications (pp. 3-12). San Diego, CA: Academic Press (Year: 1990).*
Roux, K.H. Genome Research 1995; 4: S185-S194 (Year: 1995).*
Nagai et al. Marine Genomics 2012; 7: 51-56 (Year: 2012).*
Bolch et al. Phycologia 2001; 40: 162-167 (Year: 2001).*
Hansen et al. Journal of Phycology 2000; 36: 394-410 (Year: 2000).*
Scholin et al. Journal of Phycology 1994; 30: 999-1011 (Year: 1994).*
Mertens et al. The Journal of Eukaryotic Microbiology 2013; 60: 545-563 (Year: 2013).*
"General Recommendations for DNA Electrophoresis", Thermo Fisher Scientific (2012), 2 pages (Year: 2012).*
Bolch et al. Phycologia 1997; 36: 472-478 (Year: 1997).*
Matsuoka, K. & Fukuyo, Y. (2000) Technical Guide for Modern Dinoflagellate Cyst Study. WESTPAC-HAB/WESTPAC/IOC (Year: 2000).*
Haff, L.A. PCR Methods and Applications 1994; 3: 332-337 (Year: 1994).*

* cited by examiner

SEQUENCE LISTING

```
<160> NUMBER OF SEQ ID NOS: 2

<210> SEQ ID NO 1
<211> LENGTH: 16
<212> TYPE: DNA
<213> ORGANISM: Artificial Sequence
<220> FEATURE:
<223> OTHER INFORMATION: synthetic

<400> SEQUENCE: 1
gtccgccctc tgggtg                                                    16

<210> SEQ ID NO 2
<211> LENGTH: 21
<212> TYPE: DNA
<213> ORGANISM: Artificial Sequence
<220> FEATURE:
<223> OTHER INFORMATION: synthetic

<400> SEQUENCE: 2
tcgcagtagt sygtctttaa c                                              21
```

MOLECULAR IDENTIFICATION METHOD FOR SINGLE DINOFLAGELLATE CYST

REFERENCE TO AN ELECTRONIC SEQUENCE LISTING

The contents of the electronic sequence listing (15816571 SequenceListing20180624.txt; Size: 1,000 bytes; and Date of Creation: Jun. 24, 2018) is herein incorporated by reference in its entirety.

FIELD OF THE INVENTION

The present invention relates to molecular identification technology of single dinoflagellate cyst, more specifically to a technique method for separation, cleaning, crushing of single dinoflagellate cyst, transferring of the crushed liquids of the single dinoflagellate cyst and PCR amplification.

BACKGROUND OF THE INVENTION

The dinoflagellate cyst is an important stage in the life history of dinoflagellate, it can not only promote the outbreak of red tide, but also help the dinoflagellate to survive from an unfavorable environment. According to the ecological, economic and human health effects, the dinoflagellate cysts can be divided into harmful dinoflagellate cysts (e.g. most *Alexandrium*) and harmless dinoflagellate cysts (e.g., most of the original polychaete). According to whether the dinoflagellate—produce toxins, the harmful dinoflagellate cysts can be divided into harmful toxin-producing dinoflagellate cysts (such as *Alexandrium tamarense* cyst, with thorn knee gully cyst and Prorocentrum cyst) and harmful no-toxin-producing cyst (can cause red tide, such as *Scrippsiella trochoidea, Polykrikos kofoidii* and *Polykrikos schwartzii*, etc.). According to the type of toxins contained and the hazards they cause to humans, harmful toxin-producing dinoflagellate cyst can be divided into different types, such as toxins (PSP) contained in the cyst of *Alexandrium tamarensis* causing the appearance of limbs numbness, speech impairment and other symptoms of paralysis, *Procentrum lima* contains the toxin (NSP) can cause diarrhea, etc. in humans. Therefore, the accurate identification of dinoflagellate cyst is very important. It is not only conducive to the monitoring of harmful red tide to reduce the harm caused by harmful red tide, but also conducive to the study of dinoflagellate diversity.

The identification of dinoflagellate cysts are mainly divided into morphological identification and molecular biological identification.

Morphological identification, including cyst morphology identification and morphological identification of vegetative cells after germination, according to the morphological characteristics, majority of morphological characteristics can be identified to the genus level, a few of morphological characteristics can be identified to the level of species, and identification through the germination of cyst needs a longer time, and not all cyst can germinate successfully;

Molecular biological identification is mainly based on molecular barcodes. Since barcodes in databases such as NCBI are constantly improved, so that molecular barcodes have been widely used in the field of identification of dinoflagellate cyst, and most of them can be identified to species level.

The traditional molecular identification of dinoflagellate cyst often requires the germination and proliferation of dinoflagellate cyst for the purpose of extracting nucleic acids, then the remaining experimental steps for molecular identification can be carried out. The disadvantage of this molecular identification method is time-consuming and not conducive to the rapid identification of dinoflagellate cyst, and is not suitable for ungerminated cyst and the cyst with low abundance cyst. Although Bolch et al. (2001) invented the method for molecular identification of single dinoflagellate cyst without nucleic acid extraction steps, this method is more suitable for the identification of more than two cysts and does not apply to the identification of single dinoflagellate cyst. Because of the morphological plasticity of dinoflagellate cysts and the overlap morphological characteristics of cysts, the cysts belonging to different species are mistakenly treated as the same kind of cyst for PCR amplification at the same time, which eventually leads to the inaccuracy or failure of molecular identification. Therefore, rapid molecular identification technique of the single-cyst without nucleic acid-free extraction and cyst germination still obstacles to the exact molecular identification of cysts.

SUMMARY OF THE INVENTION

The invention aims to solve the problems of the existing molecular identification of dinoflagellate cyst and provides a simple convenient method without nucleic acid extraction capable of rapid and accurate molecular identification of single dinoflagellate cyst without the germination of the cysts.

According to an embodiment of the present invention, there is provided a molecular identification method for single dinoflagellate cyst, comprising:

obtaining crushed liquids of the single dinoflagellate cyst;

performing a first PCR amplification with the crushed liquids as a template, SEQ ID No.1 GTCCGC-CCTCTGGGTG as the forward primer of an outer primer pair, and SEQ ID No.2 TCGCAGTAGTSYGTCTTTAAC as the reverse primer of the outer primer pair to obtain the PCR amplification product to determine a species of the single dinoflagellate cyst according to the first amplification product.

Optionally, determining the species of the dinoflagellate cyst according to the first amplification product, comprises:

sequencing the first amplification product and determining the species of the dinoflagellate cyst.

Optionally, when the first PCR amplification is performed, the PCR system is as follow: 10 μL crushed liquids of the dinoflagellate cyst, 2.54, buffer solution, 2.0 μL Mg2+, 20 ng the forward primer of the outer primer, 20 ng the reverse primer of the outer primer, and 1.5 U Taq enzyme.

Optionally, performing the first PCR amplification comprises:

Step a. performing the first PCR amplification at 95° C. for 5 mins;

Step b. performing a PCR amplification cycle orderly by the following parameters for 30 times: 95° C. for 30 s, 57° C. for 45 s, 72° C. for 60 s; and Step c. performing at 72° C. for 7 mins to obtain the first PCR amplification product.

Optionally, after the first PCR amplification product is obtained, further comprising:

performing gel electrophoresis on the first amplification product by agar or agarose with a mass content of 2% to observe the reactant, and if the band of the reactant fails to meet the predetermined requirement, the method further comprises:

performing a second PCR amplification and sequencing with SEQ ID No.1 GTCCGCCCTCTGGGTG as the forward primer of the inner primer and SEQ ID No.2-TCGCAGTAGTSYGTCTTTAAC as the reverse primer of the inner primer and determining the species of dinoflagellate cyst;

if the band of the reactant meets the predetermined requirement, sequencing the first amplification product directly to determine the species of the dinoflagellate cyst.

Optionally, performing the second PCR amplification comprises:

step d. performing amplification at 95° C. for 5 mins;

step e. performing the PCR amplification cycle orderly by the following parameters for 30 times:

95° C. for 30 s, 57° C. for 45 s, 72° C. for 45 s; and step f. performing at 72° C. for 7 mins to obtain the amplification product.

Optionally, it further comprises:

isolating single dinoflagellate cyst from marine sediments and storing the isolated single dinoflagellate cyst in the dark for future use;

crushing the dinoflagellate cyst;

transferring the crushed liquid of the dinoflagellate cyst into a PCR tube.

Optionally, obtaining the crushed liquid of the dinoflagellate cyst, comprises:

isolating the single dinoflagellate cyst from marine sediments;

crushing the dinoflagellate cyst to obtain the crushed liquids of the single dinoflagellate cyst.

Optionally, isolating the single dinoflagellate cyst from marine sediments comprises:

taking the sample of marine sediment, dissolving the samples in filtered seawater or artificial seawater to obtain a sample solution and performing ultrasonic treatment to the sample solution;

filtering the sample solution by a nylon mesh after ultrasonic treatment, intercepting the particulate matter, performing suspension treatment to the intercepted particulate matter and obtaining the liquids containing the suspended particle matter;

looking for single dinoflagellate cyst from the liquid containing the suspended particle matter through a microscope, absorbing the liquid containing a single dinoflagellate cyst and transferring into a PCR tube; and isolating the dinoflagellate cyst from the liquids containing a single dinoflagellate cyst.

Optionally, filtering the sample solution by a nylon mesh after ultrasonic treatment comprises:

filtering the sample solution orderly with the nylon mesh with 130 μm pore size and nylon mesh with 20 μm pore size, taking the particle matter intercepted on the nylon mesh with 20 μm pore size into a watch glass, vortexing to obtain the liquids containing the suspended particle matter.

Optionally, after isolating a single dinoflagellate cyst from the marine sediments and before crushing the dinoflagellate cyst, the method further comprises:

placing an ultrasonic probe into the PCR tube so that the bottom end of the ultrasonic probe is immersed in the liquids containing a single dinoflagellate cyst, cleaning the dinoflagellate cyst ultrasonically adopting predetermined ultrasonic power and time.

Optionally, a predetermined spacing is between the ultrasonic probe and the PCR tube.

Optionally, when the dinoflagellate cyst is *Gonyaulax, Polykrikos, Lingulodinium, Pyrophacu* and the ultrasonic power is 100 W, the ultrasonic cleaning time is less than or equal to 3 seconds.

Optionally, when the dinoflagellate cyst is an original *Protoperidinium* cyst and the ultrasonic power is 100 W, the ultrasonic cleaning time is less than or equal to 5 seconds.

Optionally, isolating the dinoflagellate cyst from a liquid containing single dinoflagellate cyst comprises:

inserting a pipette into the bottom of a liquid containing a single dinoflagellate cyst and aspirating a liquid containing a single dinoflagellate cyst onto surface of a clean glass slide;

diluting the liquid located on the surface of the glass slide with distilled water, pipetting the liquid containing a single dinoflagellate cyst into a clean place of a carrier plate, continuing to dilute with distilled water, pipetting the liquid containing a single dinoflagellate cyst to another clean place of the carrier until no impurity is observed on the periphery of the dinoflagellate cyst;

pipetting the peripheral water of the dinoflagellate cyst and air-dry the dinoflagellate cyst to obtain the dinoflagellate cyst.

Optionally, crushing the dinoflagellate cyst comprises:

taking a cover glass and cover on the top of the dinoflagellate cyst, under microscope observation, squeezing the coverslip to disintegrate the dinoflagellate cyst, and the position of the dinoflagellate cyst is marked.

Optionally, transferring the crushed liquid of the dinoflagellate cyst into a PCR tube, comprises:

rinsing the cyst fragmentation position of the cover glass slide with distilled water at least twice to obtain the crushed liquid of the dinoflagellate cyst, transferring the crushed liquid of the dinoflagellate cyst into the PCR tube.

It can be seen from the above that the present invention mainly introduces the ultrasonic technology to clean the impurity debris incidental to a single cyst to minimize or even eliminate the inhibitory effect of these impurity debris (PCR inhibitors) on PCR amplification; at the same time, two pairs of dinoflagellate specific primers are designed. For the samples with weak amplification bands and unable to be sequenced, a nested PCR method was adopted to make up for the shortcomings.

It can be seen from the above that in the embodiment of the present invention, an outer primer suitable for PCR amplification (including the forward primer and the reverse primer) is found and applied to PCR amplification of dinoflagellate cyst cells, The molecular identification of the single dinoflagellate cyst through the PCR amplification product can be realized. The technical scheme can remarkably improve the accuracy of single dinoflagellate cyst identification.

In addition, the outer primer provided by this embodiment has high versatility in the molecular identification of dinoflagellate cyst and has higher resolution among different species.

The invention can realize the molecular identification of various single dinoflagellate cyst without the need of nucleic acid extraction, the germination culture of cyst and short period of time, and the identification rate is over 85%.

BRIEF DESCRIPTION OF THE DRAWINGS

The drawings described herein are used to provide a further understanding of the present invention and constitute a part of the present application, and do not constitute improper limitations to the present invention.

Wherein, A-1 and A-2 are enlarged views before *Protoperidinium claudicans* under the microscope before and after ultrasonic cleaning respectively.

B-1 (C-1) and B-2 (C-2) are enlarged views of the *Protoperidinium leonis* before and after ultrasonic cleaning respectively.

D-1 and D-2 are enlarged views of *Gouyaulax spinifera* in the microscope before and after ultrasonic cleaning respectively.

DETAILED DESCRIPTION OF THE INVENTION

The present invention is described in detail below with reference to the accompanying drawings and specific examples. The schematic examples and descriptions of the present invention are used to explain the present invention, but not to limit the present invention.

Embodiment 1

Figure 1:
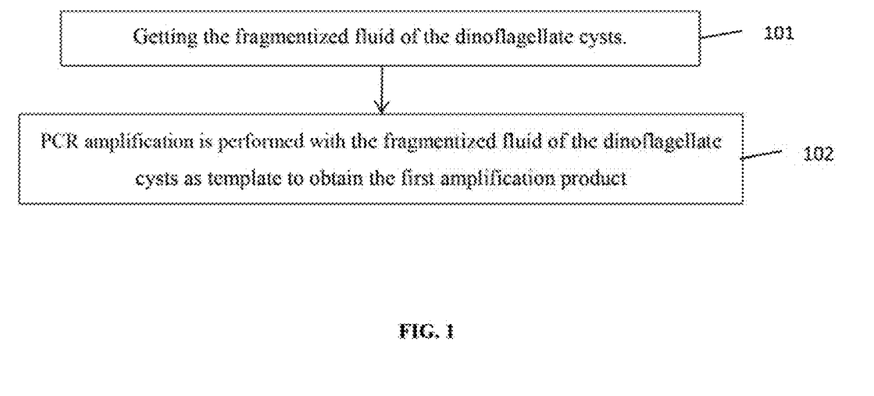
FIG. 1 is a schematic view of an identification method for dinoflagellate cyst according to embodiment 1 of the present invention.

As shown in FIG. 1, the present embodiment provides a molecular identification method for single dinoflagellate cyst, comprising the following steps:

step 101: obtaining the crushed liquid of the dinoflagellate cyst.

step 102: performing the PCR amplification using the crushed liquid of the dinoflagellate cyst as template to obtain the amplified product.

The present invention found a forward primer of outer primer (denoted as dino-18SE-F), the nucleotide sequence of dino-18SE-F is TCGCAGTAGTSYGTCTTTAAC shown as SEQ ID No.2;

the present invention found a reverse primer of outer primer (denoted as dino-18SE-R), the nucleotide sequence of dino-18SE-R is GTCCGCCCTCTGGGTG shown as SEQ ID No.1;

A Polymerase Chain Reaction (PCR) amplification marked as the first PCR amplification, is performed taking dinoflagellate cyst crushed liquid as a template and introducing the forward primer of the outer primer and the reverse primer of the outer primer to obtain the amplification product (denoted as the first amplification product).

In this step, the PCR amplification can be performed without limitations to a PCR amplification process according to the prior art.

In addition, the present inventor also gives preferred PCR amplification scheme as follows:

PCR system is: 10 µL crushed liquid of the dinoflagellate cyst, 2.54, buffer solution, 2.0 µL $Mg^{2+}$, 20 ng of forward primer of the outer primer, 20 ng of the reverse primer of the outer primer, 1.5 U Taq enzyme, and water is added into the above system to 25 µL.

PCR amplification program is as follows:

step a. the first PCR amplification was performed at 95° C. for 5 mins;

step b. the PCR amplification cycle was performed orderly by the following parameters for 30 times: 95° C. for 30 s, 57° C. for 45 s 72° C. for 60 s; and step c. elongation at 72° C. for 7 mins to obtain the first PCR amplification product.

After the reaction was completed, the first amplification product was obtained, and the first amplification product can be sequenced to determine the species of the dinoflagellate cyst, specifically, the solution of sequencing of the amplification product to determine the species of the dinoflagellate cyst can be performed based on the prior art.

It can be seen from the above that in the embodiment of the present invention, an outer primer are found, suitable for PCR amplification (including the forward primer of the outer primer and the reverse primer of the outer primer), and applied to PCR amplification of dinoflagellate cyst cells. Molecular identification of the single dinoflagellate cyst can be realized through the PCR amplification product. The technical scheme can remarkably improve the accuracy of single dinoflagellate cyst identification.

And, the outer primers provided in this embodiment have high versatility in the molecular identification of dinoflagellate cyst and have higher resolution among different species.

The invention can realize the molecular identification of a plurality of single dinoflagellate cyst without nucleic acid extraction and the germination culture of cyst in short period of time, and the identification rate is over 85%.

Embodiment 2

Figure 2:
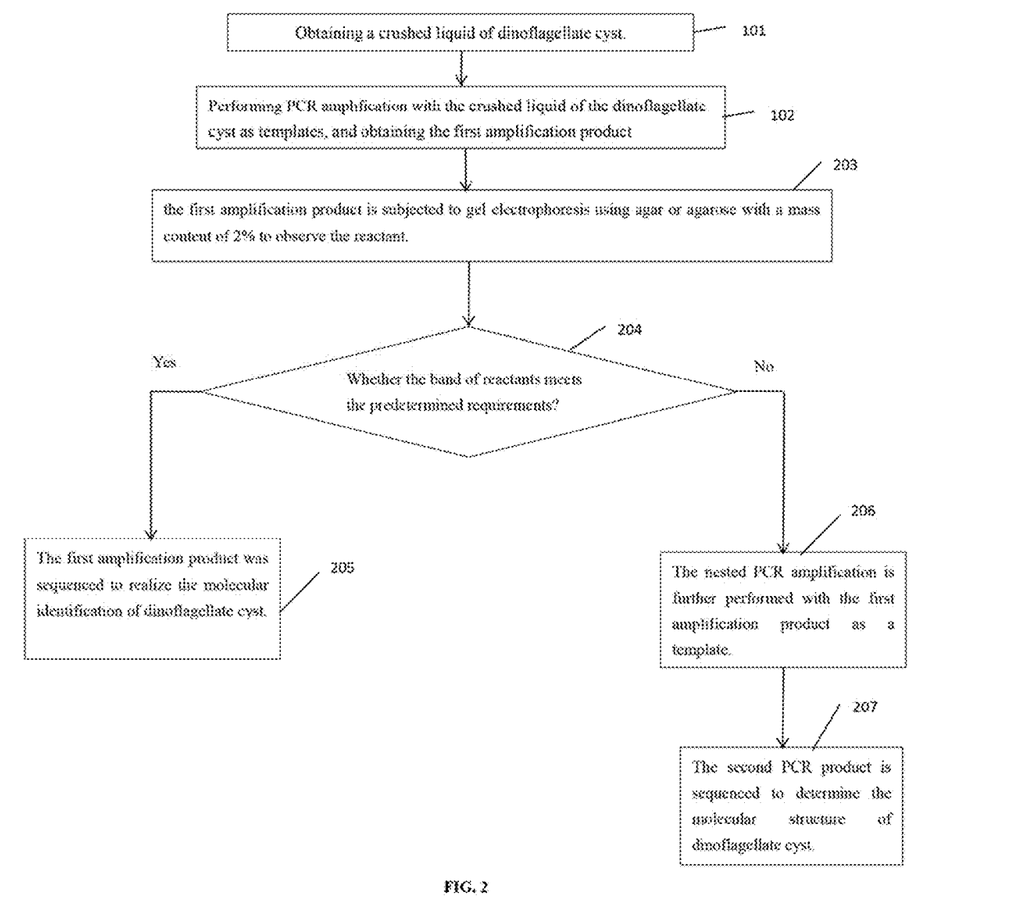
FIG. 2 is a schematic view of an identification method for dinoflagellate cyst according to embodiment 2 of the present invention.

As shown in FIG. 2, as a schematic illustration of this embodiment, the present invention also provides the following preferred technical scheme:

after the step 102 was performed in the present invention, the method further comprises:

step 203: performing gel electrophoresis with the first amplification product adopting agar or agarose with a mass content of 2%, and observing the reactants;

step 204: if the band of reactant does not meet the predetermined requirement, then step 205 was performed; otherwise, step 206 was performed.

The gel electrophoresis reaction was observed. If the band of the reactant was clear and bright, then step 205 was performed; otherwise, step 206 was performed.

Step 205: the first amplified product was sequenced to achieve molecular identification of dinoflagellate cyst.

This step can be performed as the prior art, but is not limited to the prior art.

Step 206: the first amplification product was used as a template, and further a nested-PCR amplification was performed.

The present inventor further found an inner primer, wherein the forward primer of the inner is denoted as dino-18SI-F and the nucleotide sequence of the forward primer of the inner primer is dGTCCGCCCTCTGGGTG shown as SEQ ID NO: 1; and the reverse primer of the inner primer is denoted as dino-18SI-R, the nucleotide sequence of the reverse primer of the inner primer is TCGCAGTAGTSYGTCTTTAAC shown as SEQ ID NO: 2.

The step can be performed based on the prior art.

Preferably, the present invention also provides the following preferred embodiment:

wherein, the nested-PCR system is: 1 µL the first amplification, 2.5 µL buffer solution, 2.0 µL $Mg^{2+}$, 20 ng of the forward primer of the inner primer, 20 ng of the reverse primer of the inner primer, 1.5 U Taq enzyme, and water was added to 25 µL;

PCR amplification procedure comprises:

step d. amplification was performed at 95° C. and for 5 mins;

step e. according to the following reaction temperature and reaction time for a PCR amplification cycle, performing 30 PCR amplification cycles:

95° C. for 30 s, 57° C. for 45 s, 72° C. for 45 s; and step f. elongation at 72° C. for 7 mins to obtain the amplification product.

The reaction was finished, and the PCR product was obtained (denoted as the second PCR product).

Step 207: the second PCR product was sequenced to determine the molecular structure of the dinoflagellate cyst.

The technical scheme of specific sequencing to determine the molecular structure can be based on the prior art, but is not limited to the prior art.

It can be seen from the above that in the embodiment of the present invention, an outer primer is found, suitable for PCR amplification (including the forward primer of an outer primer and the reverse primer of an outer primer), and applied to PCR amplification of dinoflagellate cyst cells. Molecular identification of the single dinoflagellate cyst can be realized through the PCR amplification product. The technical scheme can remarkably improve the accuracy of single dinoflagellate cyst identification.

In summary, in this embodiment, two pairs of specific primers (the outer primer and the inner primer) of dinoflagellate are designed. If the first amplification product is difficult to be sequenced due to weak band of gel electrophoresis product, the nested PCR amplification scheme was adopted for further amplification of the first amplification product so that the accuracy of single dinoflagellate cyst identification is improved.

Embodiment 3

As an addition to embodiment 1 and embodiment 2, the present embodiment further provides an alternative scheme of how to obtain the dinoflagellate cyst crushed liquid in step 101.

The alternative scheme is as follows, the step 101 specifically comprises:

step 1011: separating dinoflagellate cyst from marine sediments.

As a schematic illustration of this embodiment, this step may be implemented according to the following preferred technical scheme.

The marine sediment sample was taken and dissolved in filtered seawater or artificial seawater to obtain a sample solution, and the sample solution was sonicated.

The marine sediment sample was dissolved in seawater during this process so that the viability of dinoflagellate cyst in the marine sediment sample was increased and dissolved in purified water, and crushing of dinoflagellate cyst due to pressure differences between inside and outside is avoided. Therefore, dissolving the marine sediment sample in seawater was beneficial to improve the identification accuracy.

The seawater dissolved with the sample of marine sediment was sonicated, but sonication was not limited to sonicate with an ultrasonic cell disrupter type JY92-IIDN manufactured by Ningbo Xinzhi Bio Co., and specifically, the ultrasonic probe was extended into the seawater and was sonicated at a rated power ultrasound 100 W for 30 seconds.

During the ultrasonic treatment, it is preferable to avoid the problem that the ultrasonic probe touches the inner wall of the container, thereby avoiding the problem that the ultrasonic dredging effect is not good and part of the ultrasonic intensity of ultrasonic wave was too large to result in the crushing of dinoflagellate cyst.

2. The sample solution was filtered by nylon mesh after ultrasonic treatment, the particulate matter was intercepted, and the liquid containing the suspended particle matter was obtained after suspension treatment of intercepted particulate matter.

The sample solution was filtered orderly with the nylon mesh with 130 μm pore size and the nylon mesh with 20 μm pore size, the particle matter intercepted on the nylon mesh with 20 μm pore size was taken into a watch glass, the liquid containing suspended particle matter was transferred into a 1.5 ml clean centrifuge tube after vortexing the watch glass.

3. A single dinoflagellate cyst was found from the liquid containing the suspended particle matter through a microscope, the liquid containing the single dinoflagellate cyst was transferred into a PCR tube.

300 μL of the liquid containing suspended particle matter was pipetted from the centrifuge tube into a clean glass slide and the view of a single dinoflagellate cyst was found under a microscope; after a single dinoflagellate cyst was found, the larger impurity particle matter around the dinoflagellate cyst was carefully removed, the liquid containing dinoflagellate cyst was pipetted with a pipette, and transferred into a 200 μL clean PCR tube.

4. The dinoflagellate cyst was isolated from a liquid containing single dinoflagellate cyst.

Distilled water was added to the PCR tube to about 50 μL, the diameter φ2 probe of an ultrasonic cell disrupter (Ningbo Xinzhi Bio Co., model JY92-IIDN) was stretched into the PCR tube, and avoids contacting to the bottom and wall of the tube, the single dinoflagellate cyst was ultrasonic cleaned.

In the present embodiment, the present invention finds the following technical scheme for the ultrasonic cleaning of dinoflagellate cyst. By adopting the technical solution, the problem of the crushing of the dinoflagellate cyst caused by the ultrasonic cleaning can be avoided, and the thorough cleaning was ensured.

Specifically, if the present dinoflagellate cyst was the genus *Gonyaulax, Polykrikos, Lingulodinium, Pyrophacus* cysts which cystic wall structure was easy to break, the ultrasonic power was 100 W and the ultrasonic cleaning time was about 3 seconds.

If the current dinoflagellate cyst are *Protoperidinium* group which cyst wall is tough, the ultrasonic power is 100 W and the ultrasonic cleaning time was about 5 seconds.

After each ultrasonic cleaning, the bottom of the probe should be rinsed with distilled water to prevent the dinoflagellate cyst from losing the dinoflagellate cyst due to its attachment to the probe.

Step 1012: dinoflagellate cyst are broken, broken liquid of dinoflagellate cyst is obtained.

After obtaining a sonicated liquid containing a single dinoflagellate cyst, dinoflagellate cyst sink to the bottom of the PCR tube as the density of dinoflagellate cyst is greater than that of water, the liquid in the bottom of the PCR tube was pipetted to a slide with 10 μL pipette; and the liquid containing dinoflagellate cyst was diluted by adding an equal volume of distilled water, the dinoflagellate cyst was pipetted by a pipette to another position of the same slide, and the dinoflagellate cyst was diluted with the same method, until there was no significant impurities in the liquid around dinoflagellate cyst.

Subsequently, the distilled water around the dinoflagellate cyst is pipetted with a pipette and the remaining moisture around the dinoflagellate cyst was naturally air-dried.

A clean cover glass was taken over the dinoflagellate cyst directly above and the dinoflagellate cyst was in the center of the cover glass, and the cover glass was squeezed directly above the dinoflagellate cyst with a tweezer under the microscope observation, the position of the dinoflagellate cyst on the cover glass was marked after observing the broken dinoflagellate cyst.

10 μL distilled water was pipetted on the inner wall of a 200 μL clean PCR tube (lie flat) with a 10 μL pipette standby, the cover glass was removed with a tweezer and the cover glass was placed upside down on a clean desktop.

For the crushed liquid of the dinoflagellate cyst remaining on the cover glass, 2-5 μL of distilled water on the wall of the PCR tube was pipetted to the reverse side of the sign marked on the cover glass and rinsing repeatedly to transfer the washed liquid to the bottom of the PCR tube, repeating this step.

For the crushed liquid of the dinoflagellate cyst remaining on the cover slide, rinsing the crushed liquid of the dinoflagellate cyst repeatedly with the dynamic monitoring of the microscope and transferring to the bottom of the same PCR tube, the procedure can be repeated until no crushed liquid of the dinoflagellate cyst was on the slide under microscopic observation so far.

It can be seen from the above that, in the embodiment of the present invention, the single dinoflagellate cyst was rinsed to minimize or even eliminate the inhibitory effects of these impurities (PCR inhibitors) on PCR amplification.

Figure 3:
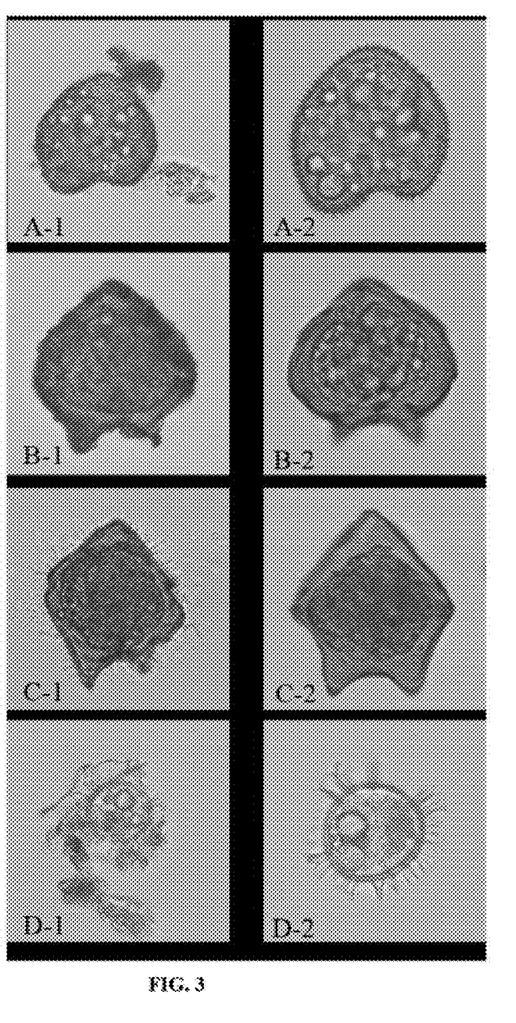
FIG. 3 is a comparison chart of the single dinoflagellate cyst before and after ultrasonic cleaning provided by Example 3 of the present invention.

FIG. 3 is a comparison effect view provided in embodiment 3 of the present invention single dinoflagellate cyst ultrasound contrast before and after washing, wherein, A-1 and A-2 are respectively enlarged views of *Protoperidinium claudicans* before and after ultrasonic cleaning; B-1 (C-1) and B-2 (C-2) are respectively enlarged views of *Protoperidinium leonis* before and after ultrasonic cleaning under the microscope; D-1 and D-2 are respectively *Gouyaulax spinifera* before and after ultrasonic cleaning under the microscope.

It can be seen from the above that the preferred technical solution of cleaning dinoflagellate cyst by using the ultrasonic wave provided by the present embodiment is to improve the accuracy of molecular identification of individual dinoflagellate cyst to equal to or greater than 90% by the PCR amplification product.

The above-mentioned embodiments do not constitute any limitation on the protection scope of the technical solutions. Any modification, equivalent replacement and improvement made within the spirit and principle of the above embodiments should be included in the protection scope of the technical solution.

What is claimed is:

1. A molecular identification method for a single dinoflagellate cyst, comprising:
    (a) dissolving a sample of a marine sediment in filtered seawater or artificial seawater to obtain a sample solution and performing ultrasonic treatment on the sample solution;
    filtering the sample solution through a nylon mesh after ultrasonic treatment, intercepting particulate matter, and performing suspension treatment on the intercepted particulate matter to obtain liquids containing suspended particle matter;
    looking for a single dinoflagellate cyst from the liquids containing suspended particle matter through a microscope, and extracting and transferring a liquid containing a single dinoflagellate cyst into a PCR tube;
    cleaning the liquid containing the single dinoflagellate cyst using ultrasonic treatment, and obtaining a crushed liquid of the single dinoflagellate cyst;
    (b) performing a first polymerase chain reaction (PCR) with the crushed liquid of the single dinoflagellate cyst as a template, SEQ ID NO: 1 (GTCCGC-CCTCTGGGTG) as a forward primer and SEQ ID NO: 2 (TCGCAGTAGTSYGTCTTTAAC) as a reverse primer according to the following procedure: incubation at 95° C. for 5 minutes; cycling 30 times with successive cycles of 95° C. for 30 seconds, 57° C. for 45 seconds and 72° C. for 60 seconds; and elongation at 72° C. for 7 minutes, so as to obtain a first amplification product;

(c) checking whether the first amplification product is a target sequence using agarose gel electrophoresis;

(d) if DNA bands obtained in the agarose gel electrophoresis of step (c) show that the first amplification product meets a predetermined requirement, sequencing the first amplification product to determine the species of the single dinoflagellate cyst; and (e) if DNA bands obtained in the agarose gel electrophoresis of step (c) show that the first amplification product fails to meet the predetermined requirement, performing a second PCR with the first amplification product as a template, SEQ ID NO: 1 (GTCCGCCCTCTGGGTG) as a forward primer and SEQ ID NO: 2 (TCGCAGTAGTSYGTCTTTAAC) as a reverse primer according to the following procedure: incubation at 95° C. for 5 minutes; cycling 30 times with successive cycles of 95° C. for 30 seconds, 57° C. for 45 seconds and 72° C. for 60 seconds; and elongation at 72° C. for 7 minutes, so as to obtain a second amplification product; and sequencing the second amplification product to determine the species of the single dinoflagellate cyst.

2. The molecular identification method of claim 1, wherein the first PCR comprises the following compositions: 10 μL of the crushed liquid of the single dinoflagellate cyst, 2.5 μL of a buffer solution, 2.0 μL of $Mg^{2+}$, 20 ng of the forward primer, 20 ng of the reverse primer, and 1.5 U Taq polymerase.

3. The molecular identification method of claim 1, wherein in step (a), the nylon mesh has a pore size of 20 μm.

* * * * *